United States Patent
Watkins

(10) Patent No.: US 6,309,622 B1
(45) Date of Patent: Oct. 30, 2001

(54) ANTIMICROBIAL DENTURE CLEANSING COMPOSITIONS

(75) Inventor: C. Douglas Watkins, Keizer, OR (US)

(73) Assignees: Protech Professional Products, Inc., Boca Raton, FL (US); Denture Dynamic Inc., Keizer, OR (US)

( * ) Notice: Subject to any disclaimer, the term of this patent is extended or adjusted under 35 U.S.C. 154(b) by 0 days.

(21) Appl. No.: 09/280,138

(22) Filed: Mar. 26, 1999

(51) Int. Cl.$^7$ ........................................................ A61L 9/04
(52) U.S. Cl. ............................ 424/44; 424/53; 252/186.26
(58) Field of Search .................. 424/44, 53; 252/186.26, 252/188.2

(56) References Cited

U.S. PATENT DOCUMENTS

| | | | |
|---|---|---|---|
| 3,671,629 | 6/1972 | Levy et al. | 424/153 |
| 4,217,234 | * 8/1980 | Krisp et al. | 252/99 |
| 4,308,252 | 12/1981 | Tomaich et al. | 424/52 |
| 4,857,224 | 8/1989 | Eoga | 252/99 |
| 5,270,032 | * 12/1993 | Pollock et al. | 424/49 |
| 5,384,062 | * 1/1995 | Eoga et al. | 252/99 |
| 5,486,304 | * 1/1996 | Eoga et al. | 252/99 |
| 5,616,782 | * 4/1997 | Thompson et al. | 560/149 |
| 5,741,487 | * 4/1998 | Asai et al. | 424/94.61 |

FOREIGN PATENT DOCUMENTS

| | | | |
|---|---|---|---|
| 2133710 | 7/1991 | (DE) | 424/53 |
| 0 248 936 A1 | 6/1986 | (EP) | 424/53 |
| 0 400 858 A2 | 5/1990 | (EP) | 424/53 |
| 2 035 363 | 10/1979 | (GB) | 424/53 |

OTHER PUBLICATIONS

The Merck Index, Merck & Co. 12th Edition, Whitehouse Station NJ, p. 1471, 1996.*

* cited by examiner

*Primary Examiner*—Ralph Gitomer

(57) ABSTRACT

A denture cleansing composition includes a monoperoxysulfate compound, an effective amount a sequestering agent, such as a citrate compound, for removal of calculus and to provide a pH to the composition in solution (water) of about 3 to 5, and an effective amount of an antimicrobial agent, such as a benzoate compound, to provide antimicrobial activity to the composition to effectively kill bacteria, or other microorganisms found on the dentures. Tests conducted show that the composition is particularly effective in killing microbial strains of *Streptococcus mutans, Streptococcus pyogenes, Candida albicans* and *Actinomyces viscosus* within 20 minutes of contact.

20 Claims, No Drawings

ANTIMICROBIAL DENTURE CLEANSING COMPOSITIONS

TECHNICAL FIELD

This invention relates to a denture cleansing composition and, more particularly, to a denture cleansing composition having improved antimicrobial activity as compared to other denture cleansing compositions. Specifically, the invention relates to a composition suitable for use as a safe and effective cleanser for dentures containing a monopersulfate compound, a sequestering agent, and an antimicrobial agent, such as a benzoate compound, which, together, effectively kill bacteria, and other microorganisms commonly found on dentures.

BACKGROUND OF THE INVENTION

Denture buildup or calculi occurs because of secretions within the mouth of the denture wearer. The parotid gland secretes material through Stenson's duct located between the first and second molars. The submandibular gland secretes additional material through Wharton's duct which is located underneath the tongue. Finally, the sublingual ducts secrete through the Rivina duct which is located on the floor of the mouth. These three glands continue to operate after the teeth have been removed. These secretions leave amylase and mucin (saliva) deposits on the dentures and cause buildup on the dentures. Of course, food particles and stains from, for example, coffee, tea and smoking also occur on dentures In order to avoid denture buildup or otherwise rid the dentures of such buildup and stains, the dentures must be cleansed from time to time. Denture cleansing is generally carried out either by brushing dentures with a paste or by soaking dentures, typically overnight, in an aqueous cleansing solution. Aqueous denture cleanser solutions are known and generally compose tablets, granules, or powders that are dissolved in water to form a cleansing bath or cleansing system in water.

Numerous denture cleansing compositions, typically provided in tablet or powder form, are well known in the art for this purpose. Traditionally, these compositions have contained a variety of sulfate salts, such as bisulfates, monopersulfates, and sulfates as detergents, oxidizers and the like, and have also utilized alkali metal and alkaline earth metal halides as bleaches. Such compositions have also included perborate, carbonate and phosphate salts in various amounts to provide effervescence and cleaning activation.

Unfortunately, the cleansing systems produced by these compositions when dissolved in water are insufficient in many respects. It is oftentimes very difficult to remove calculi and other deposits from the dentures, and effective cleansing of the dentures continues to be an extremely difficult problem in the care of dentures.

Monopersulfates such as, for example, sodium monoperoxysulfate and potassium monoperoxysulfate are well known cleansing agents often used in denture cleansing compositions. Monopersulfates are active peroxide (oxygen) bleaches which are known to be effective cleaners of organic material and may also work as a disinfectant. However, it is understood in the art that monopersulfate, including particularly potassium peroxysulfate, is most active without other agents added. Moreover, the cleaning activity of monoperoxysulfate is also selective, being much greater for organic materials. Hence, when certain other cleansing agents are added, it is well known that the cleansing activity of the monopersulfate may be reduced and, depending upon the type and amount of the additional cleansing agent added, this may significantly affect the efficacy of the composition.

For example, sequestering agents such as polyfunctional organic acids, such as citric acid, maleic acid, fumaric acid, phosphates, phosphonates, pyrophosphates, and their corresponding salts, are known to reduce the activity of the monpersulfate compound, but increases its stability. It is known that a monopersulfate compound may be decomposed by biological materials and/or by metal ions, particularly in acid solutions. Since the monopersulfate compound forms an acid in solution, the addition of a buffer such as a salt of a polyfunctional organic acid decreases the acidity of the solution, thereby prolonging the life of the monopersulfate compound. Additionally, since these salts are known to complex with metal ions, the decomposition of the monopersulfate compound is thereby further inhibited. On the other hand, addition of these salts, when added in too large of proportions start to decompose the monopersulfate rather than protect it. Thus, the proportion of the monopersulfate compound to other active agents in the composition is oftentimes considered critical to the cleansing efficacy of the composition and must be carefully controlled.

In addition, it has become increasingly known that bacteria, fungi, and other microorganisms can grow on dentures which can cause infection and reinfection problems in the oral cavity and gums of denture wearers, particularly those in nursing homes and the elderly. Among the more notable bacteria commonly found in dentures are *Candida albicans, Actinomyces viscosus, Streptococcus pyogenes,* and *Streptococcus mutans.*

Thus, the need exists for a denture cleansing composition which is effective not only as a cleanser, but also will effectively eliminate and kill bacteria, fungi, and other microorganisms in a manner which is safe to the denture wearer.

In the art, monopersulfate-containing cleanser compositions are well known. U.S. Pat. Nos. 4,857,224 and 5,486,304 both disclose such compositions. These compositions may also include a sequestering agent which functions as an additional cleanser to the extent that it reacts with the calcium present in the calculus that accumulates on dentures during the day. However, neither of these references address the need for an antimicrobial disinfectant. U.S. Pat. No. 5,486,304 does, however, indicate that sodium benzoate can be used as a lubricant and/or compression aid in an amount ranging from about 0.1 to about 0.8 percent by weight. This minor amount of benzoate is not significant enough however to provide sufficient antimicrobial activity to the composition.

SUMMARY OF INVENTION

Therefore, it is an object of the present invention to provide a safe and effective denture cleansing composition.

It is another object of the present invention to provide a denture cleansing composition, as above, which can eliminate calculus buildup.

It is still another object of the present invention to provide a denture cleansing composition, as above, that can clean without brushing.

It is still a further object of the present invention to provide a denture cleansing composition, as above, which is effective in destroying bacteria, and other microorganisms commonly found on the denture prior to cleansing.

It is yet a further object of the present invention to provide a denture cleansing composition, as above, which will effectively kill the bacteria, and microorganisms within about 20 minutes These and other objects of the present invention, as well as the advantages thereof over existing prior art relating to denture cleansing compositions, which will become apparent from the description to follow, are accomplished by the improvements hereinafter described and claimed.

In general, the present invention provides a denture cleansing composition including a monopersulfate compound; an effective amount of a sequestering agent for calculus removal and to provide the pH of the composition in solution in the range of from about 3 to about 5; and an effective amount of an antimicrobial agent to provide antimicrobial activity to the composition to effectively kill bacteria, and other microorganisms during cleansing of the dentures.

The invention also provides a denture cleansing composition including at least about 75 percent by weight of a monopersulfate compound; up to about 25 percent by weight of a sequestering agent selected from the group consisting of polyfunctional organic acids and their corresponding salts; and an effective amount of an antimicrobial agent selected from the group consisting of benzoate compounds to provide antimicrobial activity to the composition sufficient to effectively kill bacteria, or other microorganisms within about one-half hour of initiation of cleansing.

PREFERRED EMBODIMENT FOR CARRYING OUT THE INVENTION

As noted hereinabove, the present invention is directed toward an improved denture cleansing composition containing a monopersulfate compound, a sequestering agent, and an antimicrobial agent, such as a benzoate compound, which is, together, effective in killing bacteria, fungi, and other microorganisms commonly found on dentures. More particularly, the composition exhibits safe and effective cleansing of dentures while further effectively destroying bacteria, and other microorganisms commonly known to grow on dentures, including *Candida albicans, Actinomyces viscosus, Streptococcus pyogenes,* and *Streptococcus mutans.*

Preferably, the composition is in powder or granular form, although not necessarily limited thereto, and is preferably used by dissolving the powder in water to form a cleansing bath or cleansing solution. The denture cleansing action of the solution may occur by soaking the dentures in the solution overnight or for as little time as about 20 minutes At the same time, the composition must also provide effective antimicrobial activity to the cleansing solution.

Also, unlike other denture cleansing compositions, the composition of the present invention preferably is devoid of perborate compounds or other compounds known to provide effervescence and activation. The composition of the present invention provides safe and effective cleansing of the dentures as well as effective antimicrobial activity to the dentures.

The composition of the present invention includes a monopersulfate compound, preferably in an amount of at least 75 percent by weight and, more preferably, comprising from about 75 percent to about 98 percent by weight of the total cleansing composition. Most preferably, the monopersulfate compound is present in an amount ranging from about 75 to about 85 percent by weight of the total cleansing composition.

The monopersulfate compound used in the composition is preferably an alkali metal monopersulfate or an alkaline earth metal monopersulfate. A preferred salt is sodium monopersulfate or potassium monopersulfate, especially when present in the form of a triple salt compound with potassium bisulfate and potassium sulfate, e.g., $KHSO_5 \cdot KHSO_4 \cdot K_2SO_4$. This granular, stable triple potassium salt is commercially available from E.I. DuPont DeNemours & Co., Inc. and is sold in the mole ratio 2:1:1 under the trademark "OXONE". Notably, the potassium monopersulfate compound, i.e., OXONE, includes an active peroxide (oxygen) bleach which is an effective cleaner of organic material and a disinfectant. Although the potassium peroxysulfate compound is most active without other agents added, it has a known that the compound forms a strong acid in solution having a pH level of about 1.5, and, therefore, cannot be used by itself as a denture cleanser since it is possible that the composition may still be present on the dentures after rinsing and the acidity of the monopersulfate compound could cause an injury to the mouth or oral cavity of the denture wearer. In additional, the cleaning activity of monopersulfate is selective, being much greater for organic materials, and for other materials.

The composition of the present invention also includes a sequestering agent to maintain solution clarity, to promote calculus, or tartar, removal and to counteract the acidity of the monopersulfate. These sequestering agents of the present invention are preferably incorporated into the composition of the present invention in an effective amount to increase the pH of the composition in solution into the range of from about 3 to about 5 and, more preferably, from about 3 to about 4.5. In the composition of the present invention, the amount of sequestering agent employed will preferably range up to about 25 percent by weight, and preferably will fall within the range of about 1 to about 25 percent by weight, with from about 12 to about 25 percent by weight of the sequestering agent being most preferred.

Preferred sequesteringagents include polyfunctional organic acids, such as citric acid, maleic acid, fumaric acid, phosphates, phosphonates, pyrophosphates, ethylene diamine tetraacetic acid and their corresponding salts. More preferred are citrate compounds, including the alkali metal and alkali earth metal citrates. Most preferred is sodium citrate or potassium citrate.

Sodium citrate soluablizes and/or decolorizes many inorganic compounds, mainly calcium and iron deposits. More importantly, the sodium citrate acts on chemicals not affected by the monopersulfate. Thus, the cleaning action of the two ingredients mixed together is greater than either one alone because of their complementary cleaning actions.

Without being bound by theory, it is believed that the sequestering agent, e.g., sodium citrate, functions in the solution of the invention by reacting with the calcium or iron present in the calculus that accumulates on dentures. This reaction renders underlying proteinaceous material, i.e., plaque, on the dentures susceptible to attack by the monopersulfate compound also present in the solution. The monopersulfate compound in turn attacks the plaque, thereby exposing more calculus to attack by the sequestering agent. Any stains attached to the above deposits are also removed in the process.

This synergistic combination of monopersulfate compound and sequestering agent in a denture cleansing composition allows for a more complete removal of both plague and calculus on dentures. Adsorbed stains, especially those due to accumulated calculus, that had been beyond reach the single cleansing ingredients are also susceptible to removal by the composition of the present invention.

However, the combination of the two chemicals must be carefully controlled because the addition of sodium citrate reduces the activity of the peroxysulfate, but increases its stability. Thus, while potassium monopersulfate forms an acid in solution and the addition of a buffer such as sodium citrate decreases the acidity, thereby prolonging the life of the monopersulfate, too large a ratio of citrate to monopersulfate will start to decompose the monpersulfate rather than protect it. Preferably, the ratio of citrate to monopersulfate should range from about 1:3 to about 1:10. Increasing the amount of citrate beyond the 1:3 ratio could have deleterious affects on the composition.

In other words, the range of sodium citrate to effectively act with a monopersulfate compound has been determined to be preferably between about 1 percent and 25 percent by weight of sodium citrate in the total composition while the potassium monopersulfate is between about 98 percent and 75 percent.

In addition to the ingredients set forth above, the present invention also includes an antimicrobial agent in an amount effective to control microbial growth on the dentures. It has been found that a benzoate compound will provide effective antimicrobial activity to the composition to effectively reduce bacteria, and other microorganisms during cleansing of the dentures. Preferably, the antimicrobial agent will effectively kill the bacteria, fungi, or other microorganisms within about one-half hour, and more preferably, within about 20 minutes, of initiating cleansing.

The benzoate compound used in the present invention is preferably an alkali metal benzoate or an alkaline earth metal benzoate which has been found to be safe and effective against various bacteria, including but not necessarily limited to *Candida albicans, Actinomyces viscosus, Streptococcus pyogenes,* and *Streptococcus mutans.* To that end, sodium benzoate has been found to be an excellent antimicrobial agent in the range of at least about 2 percent by weight to about 4 percent by weight. While any amount of sodium benzoate effective to provide antimicrobial activity to the composition can be used in the present invention, it has been found that about 3 percent by weight is most preferred. It should also be understood that, while more than 4 percent by weight of the benzoate compound can be employed if desired, the upper limit of about 4 percent by weight is the typical maximum amount recommended for use in food or other compositions normally placed in the mouth.

It will be appreciated that the amount of sodium benzoate is significantly greater than that used in other denture cleansers as lubricants and compression aids. Heretofore, no one has recognized that a benzoate compound such as sodium or potassium benzoate would be a suitable antimicrobial agent for dentures. In fact, this invention is believed to be the first to provide an antimicrobial agent in a denture cleansing composition. It will be appreciated that some of the cleansing agents employed may, as a residual effect, provide antimicrobial activity to a denture cleanser. For example, it is well known that potassium monopersulfate will effective kill certain microorganisms and even some of the common bacteria. However, it is not particularly effective against all of the common bacteria, including particularly the Streptococcus strains commonly found on dentures.

Again, without being bound to theory, it is believed that only the presence of all three active ingredients, i.e., the monopersulfate compound, the sequestering agent, e.g., sodium citrate, and the antimicrobial agent, e.g., sodium benzoate, provides a suitable composition which when prepared in solution with water, provides the proper acidity level and the suitable means for effectively killing bacteria commonly known to grow on dentures within one-half hour of contact. More particularly, an acidity level of between 3 and 5 pH and, more preferably, of 4.5 or less, is preferred, and it has been found that, when sodium benzoate is used in this denture composition, bacteria such as *Candida albicans, Streptococcus pyogenes, Actinomyces viscosus,* and *Streptococcus mutans* are destroyed within twenty minutes of contact with the solution.

It will be appreciated that, while additional active ingredients are preferably not employed, other ingredients including but not necessarily limited to flavorings, fragrances, colorants, perfumes, pH adjustment additives, lubricants, compression aids and surface tension aids may also be employed without affecting the essential nature of the invention. For example, a suitable surface tension aid for the subject composition of the present invention includes up to about 1 percent by weight of borax.

Furthermore, flavoring can be added to the solutions if the present invention in minor amounts effective for providing a flavoring to the composition. Generally, in a 55-pound drum of the chemical composition, about one-half of a cup of sugar and mint flavoring solution is typically added. The sugar and mint flavoring solution preferably includes about one-half tablespoon of pure mint mixed with 2 cups of sugar.

A fuller understanding of the present invention will be gained from a review of the following illustrative and experimental embodiment(s) of the invention. It will be appreciated, however, that these embodiments are illustrative in nature and are in no way necessarily limiting of the scope of the invention, the invention being determined and defined by the scope and spirit of the accompanying claims.

GENERAL EXPERIMENTATION

In order to demonstrate practice of the present invention, several samples of the denture cleansing composition according to the concepts of the present invention were prepared. Each sample of the present invention includes about 85 percent potassium monopersulfate commercially available under the tradename "OXONE", about 12 percent by weight of a sequestering agent, namely sodium citrate, and about 3 percent by weight of an antimicrobial agent, namely sodium benzoate. Minor amounts of flavoring (<0.1 percent by weight) was also made a part of the composition.

Sample powders and denture chips (4 cm×0.3 cm×2 cm) of this composition were provided for testing the antimicrobial activity of the composition in solution over a period of seven days against the following four known bacteria: *Actinomyces viscosus* (ATCC 15987), *Candida albicans* (ATCC 10231), *Streptococcus mutans* (ATCC 25175), and *Streptococcus pyogenes* (ATCC 12344).

Streptococcus mutans and Streptococcus pyogenes were grown in Trypticase Soy Broth (TSB) at 35° C. for 24 hours. Candida albicans was grown in Sabouraud Dextrose Broth (SDB) at 35° C. for 72 hours and Actinomyces viscosus was grown in Actinomyces Broth (AB) at 35° C. for 72 hours. Equal volumes of the four cultures were combined to form a composite culture. The number of viable cells of each microorganism in the composite culture was determined using standard plate count methodology. 5% defibrinated Sheep's blood agar (SBA) was used for the detection of the two Streptococcus sp., Potato Dextrose Agar (PDA) for the detection of *C. albicans*, and Actinomyces Agar (AA) for the detection of A. viscosus. Plates were incubated at 35° C. for 24–48, 48–96, and 48–72 hours, respectively.

On day 0, a solution of the subject composition powder was prepared in a sterile air tight container by dissolving 1 tsp. (7g) of powder in 240 ml warm sterile distilled water with stirring for 3 minutes. Another container containing 240 ml of sterile distilled water, served as a control. The solution containing the composition and the sterile distilled water solution were left in the air tight containers at room temperature for a period of 7 days.

On each day, three denture chips were washed thoroughly with tap water, sanitized with 70% ethyl alcohol for 15 minutes, and rinsed with sterile distilled water. Three chips were inoculated on one side, at a level of approximately 108 colony forming units (cfu's) per chip and allowed to air dry at 35° C. for 15 minutes. One of the three chips was analyzed without further treatment to confirm the presence of the microorganisms. A second chip was placed in the solution containing the composition and a third in sterile distilled water for 20 minutes and then analyzed. In addition, loopfuls of solution containing the composition and the water were streaked before and after 20 minute treatment of the denture chip(s). Each of the above steps were done every day for 7 days, using the same composition and distilled water solutions for the daily treatments.

Loopfuls of each solution (present invention/composition and control/distilled water) before and after each 20 minute treatment, and the 3 denture chips, were inoculated on the above mentioned media for the 3 types of microorganism species. Plates were incubated at 35° C. and examined for presence or absence of the inoculated microorganisms at 24, 48, 72 hours and at 6 days of incubation. The same was repeated every 24 hours for up to 7 days.

The results of this experiment are set forth in Table 1.

TABLE I

Initial Microbial Checks and Antimicrobial Activity of Solutions.

| | Initial microbial check prior to 20 minute treatment (Time 0 min.) | | | Composition (after 20 min. treatment) | | Control/Water (after 20 min. treatment) | |
|---|---|---|---|---|---|---|---|
| | untreated | | Control/ | Denture | | | |
| Day | Denture chip (#1)[a] | Composition (loopful)[b] | Water (loopful)[c] | chip (#2)[d] | Loopful[e] | Denture chip (#3)[f] | Loopful[g] |
| 0 | +[h] | ng[i] | ng | ng | ng | + | ng |
| 1 | + | ng | + | ng | ng | + | + |
| 2 | + | ng | + | ng | ng | + | + |
| 3 | + | ng | + | ng | ng | + | + |
| 4 | + | ng | + | ng | ng | + | + |
| 5 | + | ng | + | ng | ng | + | + |
| 6 | + | ng | + | ng | ng | + | + |
| 7 | + | ng | + | ng | ng | + | + |

Seven day data along with 24, 48, 72 hour and 6 day observation of selective plates are shown for.
[a]Table II.
[b]Table III.
[c]Table IV.
[d]Table V.
[e]Table VI.
[f]Table VII.
[g]Table VIII.
[h]Recovered growth from all inoculated microorganisms.
[i]No growth.

TABLE II

Swabs of Inoculated Untreated Denture Chip (Chip #1) for Initial Microbial Confirmation.

| | | Visual Determination of Growth | | | |
|---|---|---|---|---|---|
| Day | Medium | 24 hr | 48 hr | 72 hr | 6 days |
| 0 | SBA | +c,d | +c,d | +c,d | +c,d |
|   | AA  | +a,b | +a,b | +a,b | +a,b |
|   | PDA | +a,b | +a,b | +a,b | +a,b |
| 1 | SBA | +c,d | +c,d | +c,d | +c,d |
|   | AA  | +a,b | +a,b | +a,b | +a,b |
|   | PDA | +a,b | +a,b | +a,b | +a,b |
| 2 | SBA | +c,d | +c,d | +c,d | +c,d |
|   | AA  | +a,b | +a,b | +a,b | +a,b |
|   | PDA | +a,b | +a,b | +a,b | +a,b |
| 3 | SBA | +c,d | +c,d | +c,d | +c,d |
|   | AA  | +a,b | +a,b | +a,b | +a,b |
|   | PDA | +a,b | +a,b | +a,b | +a,b |
| 4 | SBA | +c,d | +c,d | +c,d | +c,d |
|   | AA  | +a,b | +a,b | +a,b | +a,b |
|   | PDA | +a,b | +a,b | +a,b | +a,b |
| 5 | SBA | +c,d | +c,d | +c,d | +c,d |
|   | AA  | +a,b | +a,b | +a,b | +a,b |
|   | PDA | +a,b | +a,b | +a,b | +a,b |
| 6 | SBA | +c,d | +c,d | +c,d | +c,d |
|   | AA  | +a,b | +a,b | +a,b | +a,b |
|   | PDA | +a,b | +a,b | +a,b | +a,b |
| 7 | SBA | +c,d | +c,d | +c,d | +c,d |
|   | AA  | +a,b | +a,b | +a,b | +a,b |
|   | PDA | +a,b | +a,b | +a,b | +a,b |

Key:
+ = Growth;
ng = No Growth;
a = Actinomyces viscosus;
b = Candida albicans;
c = Streptococcus mutans;
d = Streptococcus pyogenes

TABLE III

Loopful of Composition/Solution Before 20 Minute Chip Treatment.

| | | Visual Determination of Growth | | | |
|---|---|---|---|---|---|
| Day | Medium | 24 hr | 48 hr | 72 hr | 6 days |
| 0 | SBA | ng | ng | ng | ng |
|   | AA  | ng | ng | ng | ng |
|   | PDA | ng | ng | ng | ng |
| 1 | SBA | ng | ng | ng | ng |
|   | AA  | ng | ng | ng | ng |
|   | PDA | ng | ng | ng | ng |
| 2 | SBA | ng | ng | ng | ng |
|   | AA  | ng | ng | ng | ng |
|   | PDA | ng | ng | ng | ng |
| 3 | SBA | ng | ng | ng | ng |
|   | AA  | ng | ng | ng | ng |
|   | PDA | ng | ng | ng | ng |
| 4 | SBA | ng | ng | ng | ng |
|   | AA  | ng | ng | ng | ng |
|   | PDA | ng | ng | ng | ng |
| 5 | SBA | ng | ng | ng | ng |
|   | AA  | ng | ng | ng | ng |
|   | PDA | ng | ng | ng | ng |
| 6 | SBA | ng | ng | ng | ng |
|   | AA  | ng | ng | ng | ng |
|   | PDA | ng | ng | ng | ng |
| 7 | SBA | ng | ng | ng | ng |
|   | AA  | ng | ng | ng | ng |
|   | PDA | ng | ng | ng | ng |

Key:
+ = Growth;
ng = No Growth;
a = Actinomyces viscosus;
b = Candida albicans;
c = Streptococcus mutans;
d = Streptococcus pyogenes

TABLE IV

Loopful of Composition/Solution Before 20 Minute Chip Treatment.

| | | Visual Determination of Growth | | | |
|---|---|---|---|---|---|
| Day | Medium | 24 hr | 48 hr | 72 hr | 6 days |
| 0 | SBA | ng | ng | ng | ng |
|   | AA  | ng | ng | ng | ng |
|   | PDA | ng | ng | ng | ng |
| 1 | SBA | +c,d | +c,d | +c,d | +c,d |
|   | AA  | ng | +b | +b | +b |
|   | PDA | ng | +a,b | +a,b | +a,b |
| 2 | SBA | +c,d | +c,d | +c,d | 4c,d |
|   | AA  | ng | +a,b | +a,b | +a,b |
|   | PDA | ng | +a,b | +a,b | +a,b |
| 3 | SBA | +c,d | +c,d | +c,d | +c,d |
|   | AA  | +a,b | +a,b | +a,b | +a,b |
|   | PDA | +a,b | +a,b | +a,b | +a,b |
| 4 | SBA | +c,d | +c,d | +c,d | +c,d |
|   | AA  | +a,b | +a,b | +a,b | +a,b |
|   | PDA | +a,b | +a,b | +a,b | +a,b |
| 5 | SBA | +c,d | +c,d | +c,d | +c,d |
|   | AA  | +a,b | +a,b | +a,b | +a,b |
|   | PDA | +a,b | +a,b | +a,b | +a,b |
| 6 | SBA | +c,d | +c,d | +c,d | +c,d |
|   | AA  | ng | +a,b | +a,b | +a,b |
|   | PDA | +a,b | +a,b | +a,b | +a,b |
| 7 | SBA | +c,d | +c,d | +c,d | +c,d |
|   | AA  | +a,b | +a,b | +a,b | +a,b |
|   | PDA | +a,b | +a,b | +a,b | +a,b |

Key:
+= Growth;
ng = No Growth;
a = Actinomyces viscosus;
b = Candida albicans;
c = Streptococcus mutans;
d = Streptococcus pyogenes

TABLE V

Swabs of Denture Chip (Chip #2) Treated with Cleaning Solution Containing the Present Invention for 20 Minutes.

| | | Visual Determination of Growth | | | |
|---|---|---|---|---|---|
| Day | Medium | 24 hr | 48 hr | 72 hr | 6 days |
| 0 | SBA | ng | ng | ng | ng |
|   | AA  | ng | ng | ng | ng |
|   | PDA | ng | ng | ng | ng |
| 1 | SBA | ng | ng | ng | ng |
|   | AA  | ng | ng | ng | ng |
|   | PDA | ng | ng | ng | ng |

TABLE V-continued

Swabs of Denture Chip (Chip #2) Treated with Cleaning Solution Containing the Present Invention for 20 Minutes.

| Day | Medium | Visual Determination of Growth | | | |
|---|---|---|---|---|---|
| | | 24 hr | 48 hr | 72 hr | 6 days |
| 2 | SBA | ng | ng | ng | ng |
|   | AA  | ng | ng | ng | ng |
|   | PDA | ng | ng | ng | ng |
| 3 | SBA | ng | ng | ng | ng |
|   | AA  | ng | ng | ng | ng |
|   | PDA | ng | ng | ng | ng |
| 4 | SBA | ng | ng | ng | ng |
|   | AA  | ng | ng | ng | ng |
|   | PDA | ng | ng | ng | ng |
| 5 | SBA | ng | ng | ng | ng |
|   | AA  | ng | ng | ng | ng |
|   | PDA | ng | ng | ng | ng |
| 6 | SBA | ng | ng | ng | ng |
|   | AA  | ng | ng | ng | ng |
|   | PDA | ng | ng | ng | ng |
| 7 | SBA | ng | ng | ng | ng |
|   | AA  | ng | ng | ng | ng |
|   | PDA | ng | ng | ng | ng |

Key:
+ = Growth;
ng = No Growth;
a = Actinomyces viscosus;
b = Candida albicans;
c = Streptococcus mutans;
d = Streptococcus pyogenes

TABLE VI

Loopfuls of Cleaning Solution Containing the Present Invention After 20 Minute Chip Treatment.

| Day | Medium | Visual Determination of Growth | | | |
|---|---|---|---|---|---|
| | | 24 hr | 48 hr | 72 hr | 6 days |
| 0 | SBA | ng | ng | ng | ng |
|   | AA  | ng | ng | ng | ng |
|   | PDA | ng | ng | ng | ng |
| 1 | SBA | ng | ng | ng | ng |
|   | AA  | ng | ng | ng | ng |
|   | PDA | ng | ng | ng | ng |
| 2 | SBA | ng | ng | ng | ng |
|   | AA  | ng | ng | ng | ng |
|   | PDA | ng | ng | ng | ng |
| 3 | SBA | ng | ng | ng | ng |
|   | AA  | ng | ng | ng | ng |
|   | PDA | ng | ng | ng | ng |
| 4 | SBA | ng | ng | ng | ng |
|   | AA  | ng | ng | ng | ng |
|   | PDA | ng | ng | ng | ng |
| 5 | SBA | ng | ng | ng | ng |
|   | AA  | ng | ng | ng | ng |
|   | PDA | ng | ng | ng | ng |
| 6 | SBA | ng | ng | ng | ng |
|   | AA  | ng | ng | ng | ng |
|   | PDA | ng | ng | ng | ng |
| 7 | SBA | ng | ng | ng | ng |
|   | AA  | ng | ng | ng | ng |
|   | PDA | ng | ng | ng | ng |

Key:
+ = Growth;
ng = No Growth;
a = Actinomyces viscosus;
b = Candida albicans;
c = Streptococcus mutans;
d = Streptococcus pyogenes

TABLE VII

Swabs of Denture Chip (Chip #3) Treated with Distilled Water for 20 Minutes.

| Day | Medium | Visual Determination of Growth | | | |
|---|---|---|---|---|---|
| | | 24 hr | 48 hr | 72 hr | 6 days |
| 0 | SBA | +c,d | +c,d | +c,d | +c,d |
|   | AA  | +a,b | +a,b | +a,b | +a,b |
|   | PDA | +a,b | +a,b | +a,b | +a,b |
| 1 | SBA | +c,d | +c,d | +c,d | +c,d |
|   | AA  | +a,b | +a,b | +a,b | +a,b |
|   | PDA | +a,b | +a,b | +a,b | +a,b |
| 2 | SBA | +c,d | +c,d | +c,d | +c,d |
|   | AA  | +a,b | +a,b | +a,b | +a,b |
|   | PDA | +b | +b | +b | +b |
| 3 | SBA | +c,d | +c,d | +c,d | +c,d |
|   | AA  | +a,b | +a,b | +a,b | +a,b |
|   | PDA | +a,b | +a,b | +a,b | +a,b |
| 4 | SBA | +c,d | +c,d | +c,d | +c,d |
|   | AA  | +a,b | +a,b | +a,b | +a,b |
|   | PDA | +a,b | +a,b | +a,b | +a,b |
| 5 | SBA | +c,d | +c,d | +c,d | +c,d |
|   | AA  | +a,b | +a,b | +a,b | +a,b |
|   | PDA | +a,b | +a,b | +a,b | +a,b |
| 6 | SBA | +c,d | +c,d | +c,d | +c,d |
|   | AA  | +a,b | +a,b | +a,b | +a,b |
|   | PDA | +a,b | +a,b | +a,b | +a,b |
| 7 | SBA | +c,d | +c,d | +c,d | +c,d |
|   | AA  | +a,b | +a,b | +a,b | +a,b |
|   | PDA | +a,b | +a,b | +a,b | +a,b |

Key:
+ = Growth;
ng = No Growth;
a = Actinomyces viscosus;
b = Candida albicans;
c = Streptococcus mutans;
d = Streptococcus pyogenes

TABLE VIII

Loopful of Distilled Water After 20 Minute Chip Treatment.

| Day | Medium | Visual Determination of Growth | | | |
|---|---|---|---|---|---|
| | | 24 hr | 48 hr | 72 hr | 6 days |
| 0 | SBA | ng | ng | ng | ng |
|   | AA  | ng | ng | ng | ng |
|   | PDA | ng | ng | ng | ng |
| 1 | SBA | +c,d | +c,d | +c,d | +c,d |
|   | AA  | ng | +a | +a | +a |
|   | PDA | +a,b | +a,b | +a,b | +a,b |
| 2 | SBA | +c,d | +c,d | +c,d | +c,d |
|   | AA  | ng | +a | +a | +a |
|   | PDA | +a,b | +a,b | +a,b | +a,b |
| 3 | SBA | +c,d | +c,d | +c,d | +c,d |
|   | AA  | +a,b | +a,b | +a,b | +a,b |
|   | PDA | +a,b | +a,b | +a,b | +a,b |
| 4 | SBA | +c,d | +c,d | +c,d | +c,d |
|   | AA  | +a,b | +a,b | +a,b | +a,b |
|   | PDA | +a,b | +a,b | +a,b | +a,b |
| 5 | SBA | +c,d | +c,d | +c,d | +c,d |
|   | AA  | +a,b | +a,b | +a,b | +a,b |
|   | PDA | +a,b | +a,b | +a,b | +a,b |
| 6 | SBA | +c,d | +c,d | +c,d | +c,d |
|   | AA  | +a,b | +a,b | +a,b | +a,b |
|   | PDA | +a,b | +a,b | +a,b | +a,b |

TABLE VIII-continued

Loopful of Distilled Water After 20 Minute Chip Treatment.

| | | Visual Determination of Growth | | | |
|---|---|---|---|---|---|
| Day | Medium | 24 hr | 48 hr | 72 hr | 6 days |
| 7 | SBA | +c,d | +c,d | +c,d | +c,d |
| | AA | +a,b | +a,b | +a,b | +a,b |
| | PDA | +a,b | +a,b | +a,b | +a,b |

Key:
+ = Growth;
ng = No Growth;
a = Actinomyces viscosus;
b = Candida albicans;
c = Streptococcus mutans;
d = Streptococcus pyogenes All inoculated microorganisms used to contaminate the denture chips (chip #1) were recovered from untreated samples; thus, confirming initial inoculation.

Inoculated microorganisms were not recovered from the denture chip containing the present invention(chip #2) after 20 minute treatments to a working strength solution (containing present invention) for a period of seven days In contrast, all inoculated microorganisms were recovered from the denture chip (chip #3) after 20 minute exposure to distilled water at all time points.

The solution containing the composition of the present invention itself, before and after the 20 minute chip treatment, was negative for all organisms for a period of seven days. In comparison, the distilled water before the first 20 minute chip treatment was negative; but thereafter, all microorganisms (before and after treatment) were recovered on days 1 through 7.

As a result, it is believed evident that a solution of the composition of the present invention exhibited antimicrobial activity for seven days. The solution inactivated daily inoculations of *Streptococcus mutans*, *Streptococcus pyogenes*, *Candida albicans* and *Actinomyces viscosus* for a period of 7 days.

In addition to the foregoing tests, additional testing was performed using water which "just meets" the chemical standards for safe drinking water, which was specially prepared for this testing procedure. Essentially the same test was repeated using non-sterile glassware and the "worst case" tap water, and a solution was prepared using the composition of the present invention. As a result of this additional seven-day study, no organisms were recovered from the solution containing the composition of the present invention. This demonstrates (a) total kill of the organisms on the chip itself and (b) total kill of any organisms freed into the wash solution. The use of the specially prepared water, representing "worst case" tap water, did not adversely affect the antimicrobial activity of the solution of the present invention.

Thus it should be evident that the compositions and solutions of the present invention are highly effective in killing bacteria, fungi, and other microorganisms found on dentures. The invention is particularly suited for powders which are dissolved in water to provide wash solutions for cleansing of the dentures, but is not necessarily limited thereto. The compositions and solutions of the present invention can be used separately for other purposes where certain bacteria, fungi or microorganisms are known to grow.

Based upon the foregoing disclosure, it should now be apparent that the use of the denture cleansing composition described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, monopersulfate compound according to the present invention should not necessarily be limited to potassium monoperoxysulfate. Moreover, as noted hereinabove, other sequestering agents besides sodium citrate can be used and other benzoate compounds can be substituted for the sodium benzoate disclosed herein as an antimicrobial agent. Thus, the scope of the invention shall include all modifications and variations that may fall within the scope of the attached claims.

What is claimed is:

1. A denture cleansing composition comprising:
   a monopersulfate compound;
   an effective amount of a sequestering agent for calculus removal and to provide a pH of the composition in solution in the range of from about 3 to about 5; and
   an effective amount of an antimicrobial agent to provide antimicrobial activity to the composition to effectively kill bacteria and other microorganisms during cleansing of dentures, wherein said denture cleansing composition is devoid of perborate compounds.

2. The denture cleansing composition according to claim 1, wherein said monopersulfate compound is selected from the group consisting of alkali metal monopersulfates and alkali earth metal monopersulfates.

3. The denture cleansing composition according to claim 2, wherein said monopersulfate compound is selected from the group consisting of potassium monopersulfate and sodium monopersulfate.

4. The denture cleansing composition according to claim 1, wherein said sequestering agent is selected from the group consisting of polyfunctional organic acids and their corresponding salts.

5. The denture cleansing composition according to claim 4 wherein said sequestering agent is a salt of citric acid.

6. The denture cleansing composition according to claim 5, wherein said salt is selected from the group consisting of sodium citrate and potassium citrate.

7. The denture cleansing composition according to claim 1 wherein said antimicrobial agent is selected from the group consisting of benzoate compounds.

8. The denture cleansing composition according to claim 7 wherein said benzoate compound is sodium benzoate.

9. The denture cleansing composition according to claim 1, further comprising sugar and a mint flavoring solution.

10. A denture cleansing composition comprising:
    at least about 75 percent by weight of a monopersulfate compound;
    up to about 25 percent by weight of a sequestering agent selected from the group consisting of polyfunctional organic acids and their corresponding salts; and
    an effective amount of an antimicrobial agent selected from the group consisting of benzoate compounds to provide antimicrobial activity to the composition sufficient to effectively kill bacteria and other microorganisms within about one-half hour of initiation of cleansing, wherein said denture cleansing composition is devoid of perborate compounds.

11. The denture cleansing composition according to claim 10, wherein said monopersulfate compound is selected from the group consisting of alkali metal monopersulfates and alkali earth metal monopersulfates.

12. The denture cleansing composition according to claim 11, wherein said monopersulfate compound is selected from the group consisting of potassium monopersulfate and sodium monopersulfate.

13. The denture cleansing composition according to claim 10, wherein sequestering agent is the salt of citric acid.

14. The denture cleansing composition according to claim 13, wherein said salt is selected from the group consisting of sodium citrate and potassium citrate.

15. The denture cleansing composition according to claim 10, wherein said benzoate compound is sodium benzoate.

16. The denture cleansing composition according to claim 10, wherein the composition includes from about 75 to about 98 percent by weight of said monopersulfate compound; from about 1 to about 25 percent by weight of said sequestering agent; and at least about 2 percent by weight of said benzoate compound.

17. The denture cleansing composition according to claim 10, wherein the composition includes from about 75 to about 85 percent by weight of said monopersulfate, said monopersulfate being selected from the group consisting of sodium monopersulfate and potassium monopersulfate;

from about 12 to about 25 percent by weight of said sequestering agent, said sequestering agent being selected from the group consisting of sodium citrate and potassium citrate; and from about 2 to about 4 percent by weight of a benzoate compound, said benzoate compound being selected from the group consisting of sodium benzoate and potassium benzoate.

18. The denture cleansing composition according to claim 17, further comprising about one-half cup of sugar and mint flavoring solution per 55 pound of the total cleansing composition, wherein said mint flavoring solution contains about one-half tablespoon of pure mint mixed with 2 cups of sugar.

19. The denture cleansing composition according to claim 10, wherein said composition will effectively kill microbial strains of *Streptococcus mutans, Streptococcus pyogenes, Candida albicans* and *Actinomyces viscosus* during cleansing.

20. The denture cleansing composition according to claim 19 where said strains are killed within 20 minutes of contact with said composition.

* * * * *